US010359391B2

(12) United States Patent
Brown et al.

(10) Patent No.: US 10,359,391 B2
(45) Date of Patent: Jul. 23, 2019

(54) SENSOR WITH A MEMBRANE HAVING FULL CIRCUMFERENTIAL ADHESION (71) Applicant: e-SENS, Inc., Salt Lake City, UT (US)

(72) Inventors: Richard B. Brown, Salt Lake City, UT (US); Ondrej Novak, North Salt Lake, UT (US)

(73) Assignee: e-SENS, Inc., Salt Lake City, UT (US)

( * ) Notice: Subject to any disclaimer, the term of this patent is extended or adjusted under 35 U.S.C. 154(b) by 231 days.

(21) Appl. No.: 15/204,371

(22) Filed: Jul. 7, 2016

(65) Prior Publication Data
US 2018/0011046 A1 Jan. 11, 2018

(51) Int. Cl.
G01N 27/333 (2006.01)
(52) U.S. Cl.
CPC .................. G01N 27/3335 (2013.01)
(58) Field of Classification Search
CPC .................. G01N 27/333; G01N 27/3335
See application file for complete search history.

(56) References Cited

U.S. PATENT DOCUMENTS

| 4,388,167 A * | 6/1983 | Ono .................. G01N 27/333 204/419 |
| 5,900,128 A * | 5/1999 | Gumbrecht ........ G01N 27/4141 204/414 |
| 6,764,652 B2 | 7/2004 | Hower et al. |
| 7,438,851 B2 | 10/2008 | Hower et al. |
| 7,988,838 B2 | 8/2011 | Dipiazza et al. |
| 2002/0011408 A1* | 1/2002 | Lee .................. G01N 27/333 204/414 |
| 2003/0201192 A1* | 10/2003 | Prince .............. G01N 33/48785 205/775 |

(Continued)

FOREIGN PATENT DOCUMENTS

| EP | 1353751 | 4/2011 |
| JP | 2001-147215 | 5/2001 |
| JP | 2002-131275 | 5/2002 |

(Continued)

OTHER PUBLICATIONS

PCT International Search Report and Written Opinion in PCT International Application U.S. Appl. No. PCT/US2017/041098 dated Sep. 27, 2017.

(Continued)

Primary Examiner — Edward J. Schmiedel
(74) Attorney, Agent, or Firm — Alliance IP, LLC (57) ABSTRACT Embodiments are directed to a chemical sensor and a method of fabricating a chemical sensor that includes a membrane having full circumferential adhesion. The chemical sensor device includes a silicon substrate comprising a sensor-side and a backside. The sensor-side includes a sensor-side electrode; a first passivation layer disposed on the substrate; and a second passivation layer on the first passivation layer and adjacent to the sensor-side electrode, the passivation layer comprising an adhesion trench exposing a portion of the first passivation layer, and a polyimide ring disposed on the second passivation layer. The backside includes a backside electrode on the backside of the substrate. The substrate includes an electrically isolated doped region, such as a through silicon via, electrically connecting the sensor-side electrode and the backside electrode.

22 Claims, 9 Drawing Sheets (56) References Cited

U.S. PATENT DOCUMENTS

2004/0163949 A1* 8/2004 Sorensen ............ G01N 27/301
   204/280
2008/0308418 A1 12/2008 Dipiazza et al.

FOREIGN PATENT DOCUMENTS

| JP | 2008-191058 | 8/2008 |
| KR | 2003-0014527 | 2/2003 |
| WO | WO 2002/058846 | 8/2002 |

OTHER PUBLICATIONS

Franklin, Robert K. et al., "2.12 Chemical Sensors", The University of Michigan Ann Arbor, MI, Sensicore, Inc., Ann Arbor, MI, The University of Utah, Salt Lake City, UT, Elsevier B.V., 2008 (pp. 432-461) (29 pages).

* cited by examiner

SENSOR WITH A MEMBRANE HAVING FULL CIRCUMFERENTIAL ADHESION

TECHNICAL FIELD

This disclosure pertains to membrane adhesion trenches, and more particularly, to a chemical sensor with a membrane having full circumferential adhesion to a substrate.

BACKGROUND

Chemical sensors can be fabricated using semiconductor technology. The use of semiconductor manufacturing can result in a reduction of size of the chemical sensor as well as mass fabrication of chemical sensors, thereby reducing per unit cost of each sensor. More generally, the use of semiconductor manufacturing to manufacture sensors produces the same or similar benefits as it does for electrical circuits: low cost per sensor, small size, and highly reproducible behavior. Semiconductor manufacturing also facilitates the integration of signal conditioning, compensation circuits and actuators, i.e., entire sensing and control systems, which can dramatically improve sensor performance for little increase in cost.

Semiconductor manufacturing technology also provides precise control of layer thickness and lateral dimensions, so that the sensors can be miniaturized, and so that they will have well-controlled characteristics. By making the sensors small, one can calibrate them with small volumes of calibration solution. Sample volumes can be small (which may not be important in testing water, but may be important in testing other solutions, such as blood samples from newborns). Operation of the sensors also requires rinsing between samples, and storage in a controlled solution. Volumes of all of these solutions can be smaller if the sensors are miniaturized, as they are on the silicon substrates.

SUMMARY

Chemical sensors, such as ion selective electrodes (ISEs), can be made using ionophore-doped polymeric membranes. Polymeric membranes do not adhere well to silicon nitride surfaces that are often used to insulate silicon dies and to protect the silicon and other conducting layers from the solution under test and from the internal filling solution that is between the electrode and the membrane. Silicon dioxide provides a higher level of adhesion for the polymeric membranes than silicon nitride. Silicon dioxide, however, absorbs water, making it a poor encapsulant for the electronics. This disclosure describes the adhesion of a polymeric membrane to the surface of a solid-state liquid chemical sensor, thereby making the sensor more reliable and robust, and giving the sensor a longer lifetime.

Aspects of the embodiments are directed to a sensor device. The sensor device can be an ion selective chemical sensor. The sensor device may include a substrate comprising a sensor-side and a backside. The sensor-side can include a sensor-side electrode; a first passivation layer disposed on the substrate; and a second passivation layer on the first passivation layer and adjacent to the sensor-side electrode, the second passivation layer comprising an adhesion trench exposing a portion of the first passivation layer. The backside may include a backside electrode on the backside of the substrate. The substrate can include a through-silicon via (TSV) electrically connecting the sensor-side electrode and the backside electrode.

Aspects of the embodiments are directed to a sensor device. The sensor device can be an ion selective chemical sensor. The sensor device may include a substrate comprising a sensor-side and a backside. The sensor side may include a sensor-side electrode; a first passivation layer disposed on the substrate; and a second passivation layer on the first passivation layer and adjacent to the sensor-side electrode, the second passivation layer comprising an adhesion trench exposing a portion of the first passivation layer, and a polyimide ring disposed on the second passivation layer. The backside may include a backside electrode on the backside of the substrate. The substrate may include a through-silicon via (TSV) electrically connecting the sensor-side electrode and the backside electrode.

Aspects of the embodiments are directed to a method for forming a sensor device. The method may include providing a silicon substrate, the silicon substrate comprising an electrically isolated doped region (electrically isolated from the substrate with an SiO, the silicon substrate further comprising a front side and a backside, the front side comprising a front side passivation layer, and the backside comprising a backside passivation layer; etching a portion of the backside passivation layer to expose a portion of the electrically isolated doped region on the backside of the silicon substrate; forming a backside electrode over the electrically isolated doped region of the backside of the silicon substrate; etching a portion of the front side passivation layer to expose a portion of the electrically isolated doped region on the front side of the silicon substrate; forming a front side electrode on the portion of the electrically isolated doped region exposed on the front side of the silicon substrate; forming a second passivation layer on at least a portion of the front side first passivation layer; etching a trench in the second passivation layer around the sensor-side electrode to expose a portion of the front side passivation layer; forming a first ring (e.g., an SU-8 or polyimide or other material ring) between the trench and sensor-side electrode; and forming a second ring (e.g., an SU-8 or polyimide or other material ring) around the trench.

In some embodiments, the first passivation layer comprises silicon dioxide.

In some embodiments, the second passivation layer comprises silicon nitride and optionally, silicon dioxide.

In some embodiments, the sensor-side electrode comprises silver chloride on silver.

In some embodiments, the backside electrode comprises gold.

In some embodiments, the TSV comprises p-type doped silicon insulated from the rest of the substrate.

In some embodiments, the first ring defines a first diameter, and wherein the adhesion trench defines a second diameter greater than the first diameter.

Some embodiments may also include a hydrogel buffer solution disposed on the sensor-side electrode within the polyimide ring.

In some embodiments, the polyimide ring is a first polyimide ring, the sensor device comprising a second polyimide ring surrounding the adhesion trench and the first polyimide ring.

Some embodiments may also include a polymeric membrane covering the adhesion trench and contained within the second polyimide ring.

In some embodiments, the polymeric membrane comprises ionophores.

In some embodiments, the polymeric membrane comprises an ion selective membrane.

In some embodiments, the polymeric membrane contacts the first passivation layer within the adhesion trench.

Some embodiments may also include one or more adhesion layers disposed on the portion of the first passivation layer exposed within the adhesion trench, wherein the polymeric membrane is in contact with the adhesion layer.

Some embodiments may also include forming a hydrogel internal buffer on the front side electrode within the first polyimide ring.

Some embodiments also include forming a polymeric membrane over the sensor-side electrode, in the trench, and within the second polyimide ring.

In some embodiments, forming the sensor-side electrode may also include forming a platinum layer on the electrically isolated doped region exposed on the front side of the silicon substrate; forming a silver layer on the platinum layer; and forming a silver chloride layer on the silver layer.

In some embodiments, the substrate comprises one of silicon or glass or ceramic.

DETAILED DESCRIPTION

Chemical sensors, such as ion selective electrodes (ISEs) can be made using ionophore-doped polymeric membranes. For example, an ISE can use an ion-selective polymeric membrane that contains the ionophore Valinomycin for detecting potassium, or 4-tert-Butylcalix[4]arene-tetraacetic acid tetraethyl ester for detecting sodium. The ionophore is a selective binding site for the analyte. The polymeric membrane establishes a barrier between the sensor electrode and an analyte solution. The polymeric membrane facilitates the introduction of an analyte to the ionophore, which binds the charged ion, creating a charge separation between the interior of the polymeric membrane and the external aqueous solution. The charge separation can be measured to determine the presence of the specific analyte.

Polymeric membranes do not adhere well to silicon nitride surfaces that are often used to insulate the silicon and to protect the silicon and other conducting layers from the solutions under test and from the internal filling solution that is between the electrode and the membrane. Additionally, polymeric membranes adhere better to silicon dioxide than to silicon nitride.

In this disclosure, a trench is formed in the protective silicon nitride to expose the silicon dioxide passivation layer. The trenches surround the entirety of the silver/silver chloride electrode. The polymeric membrane can be deposited on the electrode (or on the hydrogel buffer solution) to form a seamless membrane attached to the adhesion ring around the entire electrode. Electrical contact to the silver/silver chloride electrode is made with a conductive via (e.g., a through-silicon via) through the silicon substrate, from sensor-side to backside.

By using a backside electrode electrically coupled to the silver/silver electrode through a via, the trench (also referred to herein as an adhesion trench) can completely encircle the active sensor, thereby minimizing areas in which there is poor adhesion of the membrane to the surface. Polyimide, SU-8, or other high-aspect-ratio photopolymers can be used to form structures (e.g., polyimide rings) to "contain" the deposited membrane cocktail (e.g., through surface tension).

Figure 1:
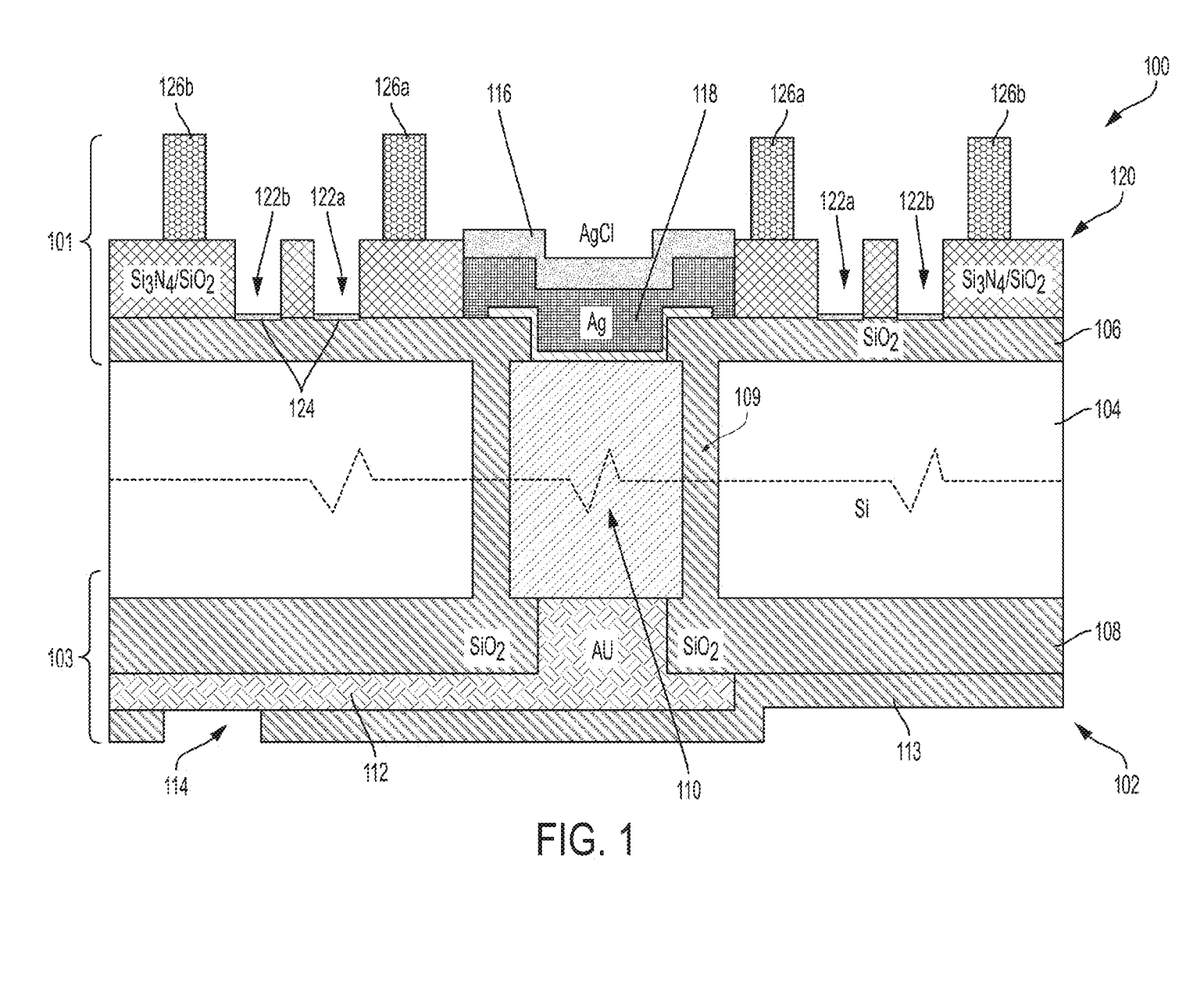
FIG. 1 is a schematic diagram of a sensor device in accordance with embodiments of the present disclosure.

FIG. 1 is a schematic diagram of a sensor device 100 in accordance with embodiments of the present disclosure. The schematic diagram shown in FIG. 1 is not drawn to scale, as a scaled illustration would minimize device architecture. Sensor device 100 includes a substrate 102. Substrate 102 can include silicon 104, such as silicon <100>. The substrate 102 includes a "sensor-side" 101 and a "backside" 103. The sensor-side 101 can include a sensor-side first passivation layer 106, which can be a silicon dioxide ($SiO_2$) layer 106. The substrate backside 103 can also include a backside passivation layer 108, which can be silicon dioxide 108. The term "layer" is used throughout this disclosure and is meant to include one or more layers of a material, and is not limited to meaning a monolayer or single atomic layer of a material.

The silicon substrate 102 can be doped to make it conductive, or can include an electrically isolated doped region 110. The electrically isolated doped region 110 can include a p-type dopant, such as a boron p-type dopant. The sensor device 100 includes sensor-side electrode 116 and a backside electrode 112. The electrically isolated doped region 110 can electrically connect the sensor-side electrode 116 with the backside electrode 112 and can be electrically isolated from the rest of the substrate by a passivation layer (e.g., SiO2 layer 109). This electrically isolated doped region 110 can be referred to as a via 110.

The backside electrode 112 can include a conductive material, such as a metal. In some embodiments, the backside electrode 112 may include gold (Au). The backside electrode 112 can be accessed by a bonding pad 114. In some embodiments, another backside passivation layer 113 can be deposited over the backside electrode to protect the backside 103 from damage. The backside passivation layer 113 can include silicon nitride or silicon dioxide.

The sensor-side 101 can include a sensor-side electrode 116. The via 110 is physically and electrically connected to the sensor-side electrode 116. The sensor-side electrode can include silver (Ag) and silver chloride (AgCl). Silver chloride has a stable interfacial potential to the internal filling solution and desirable Ohmic properties.

In some embodiments, the via 110 is electrically and physically connected to a thin platinum disc 118. The platinum disc 118 can be completely covered by silver. The silver has a chloridized surface, resulting in a silver/silver-chloride electrode.

On the sensor-side first passivation layer 106, is a sensor-side second passivation layer 120. The sensor-side second passivation layer 120 can include silicon nitride ($Si_3N_4$) and silicon dioxide ($SiO_2$). As an example, the sensor-side second passivation layer 120 can be silicon nitride, or can include a layer of silicon dioxide on top of silicon nitride.

In some embodiments, adjacent to the sensor-side electrode 116 is a polyimide ring structure 126a residing on the sensor-side second passivation layer 120. The polyimide ring 126a can be circular or substantially circular, and surround the sensor-side electrode 116.

An adhesion trench 122a can be etched into the sensor-side second passivation layer 120 adjacent to the polyimide ring structure 126a. The adhesion trench 122a can be a first adhesion trench 122a; multiple adhesion trenches, such as the second adhesion trench 122b can be formed adjacent to the first adhesion trench 122a. The first and second adhesion trenches 122a and 122b can be circular or substantially circular and can surround the sensor-side electrode 116 (and in some embodiments, surround the polyimide ring 126a).

The adhesion trenches 122a and 122b are etched to expose the underlying sensor-side first passivation layer 106 (i.e., the silicon dioxide 106). As mentioned above, polymeric membranes demonstrate higher adhesion to the silicon dioxide 106 than they would to the silicon nitride of the sensor-side second passivation layer 120. The adhesion trenches 122a and 122b can thus facilitate polymeric membrane adhesion to the sensor device 100. In some embodiments, one or more adhesion promotion layers 124 can be added to the silicon dioxide surface 106 to promote polymeric membrane adhesion. The adhesion promotion layers 124 can include silane (SiH4) or silanol. The shape of the adhesion trenches 122a and 122b may also provide mechanical adhesion of the membrane to the substrate.

In some embodiments, a second polyimide ring 126b can reside on the sensor-side second passivation layer 120. The second polyimide ring 126b can be circular or substantially circular and can surround the sensor-side electrode 116 and the adhesion trench 122a (and 122b or others, if present).

Though described as a silicon substrate, substrate 102 could in some embodiments be composed of glass or ceramic or other suitable material.

Figure 2:
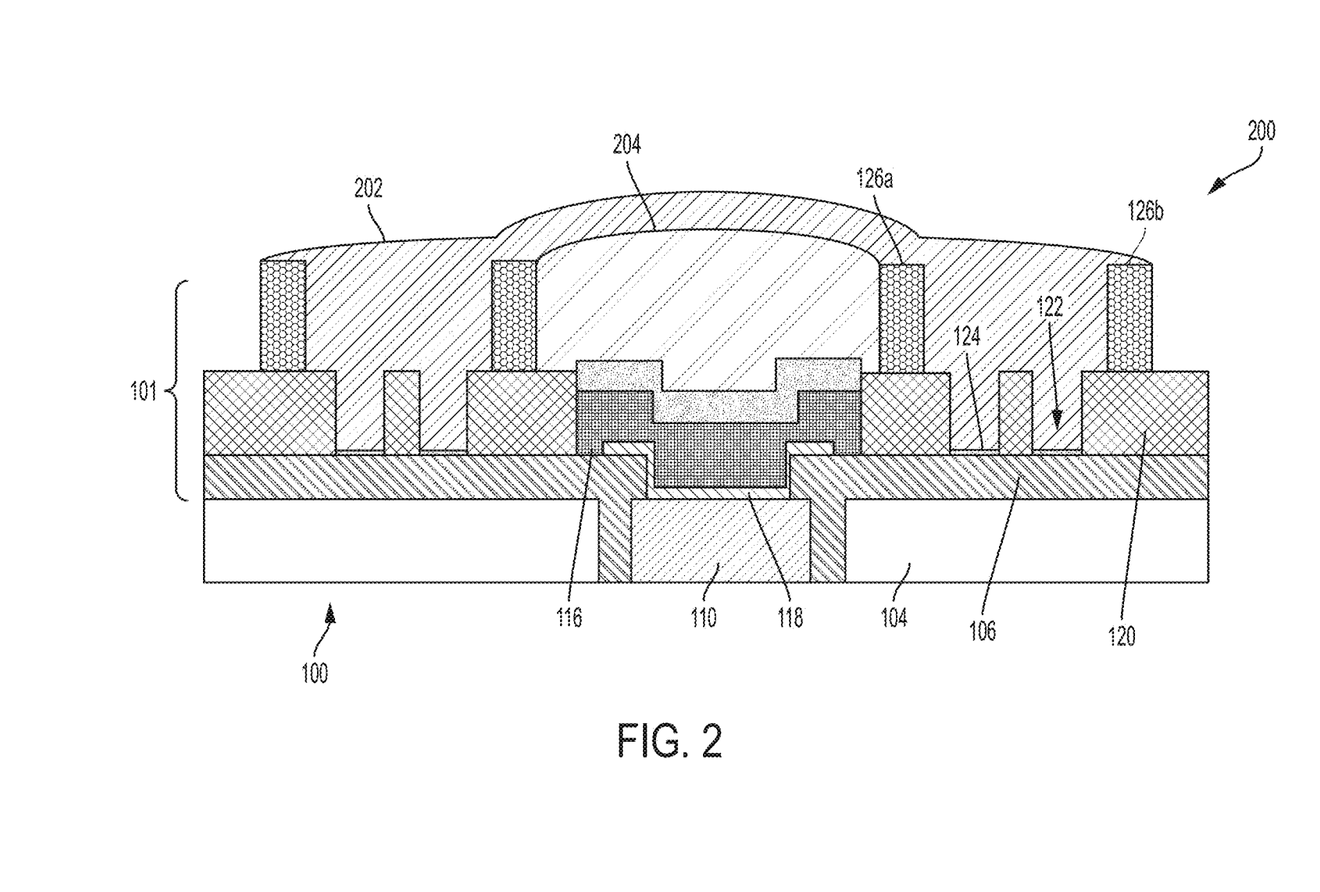
FIG. 2 is a schematic diagram of a sensor device that includes a polymeric membrane in accordance with embodiments of the present disclosure.

FIG. 2 is a schematic diagram 200 of a sensor device 100 that includes a polymeric membrane 202 in accordance with embodiments of the present disclosure. The diagram 200 of FIG. 2 shows the sensor device 100 of FIG. 1 with the addition of the polymeric membrane 202 as well as the hydrogel buffer solution 204. In FIG. 2, the first polyimide ring 126a can be shown to define the size of the hydrogel buffer solution 204. The outer polyimide ring 126b defines the size of the polymeric membrane 202 that acts as the transducer of the sensor device 100.

Also shown in FIG. 2 is the polymeric membrane 202 filling adhesion trenches 122a and 122b, and adhering to the adhesion promotion layer 124 on the silicon dioxide passivation layer 106. The polymeric membrane 202 can be "confined" by the second polyimide ring 126b based on the shape of the polyimide ring and based on surface tension of the deposited polymeric membrane cocktail solution, composed of the membrane components and organic solvent.

The polymeric membrane 202 is shown to contact the hydrogel buffer solution 204. The hydrogel buffer solution 204 can reside within the first polyimide ring 126a and contact the electrode 116. The hydrogel buffer solution 204 can stabilize the potential between the polymeric membrane 202 and the electrode 116. To provide a well-poised electrical contact to the polymeric membrane 202, a hydrogel buffer solution 204 can be used between the silver/silver chloride electrode 116 and the polymeric membrane 202. This hydrogel-based filling solution 204 is buffered with high concentrations of salts. The polymeric membrane 202 hydrates when exposed to aqueous solutions, and the high salt content of the hydrogel buffer solution 204 can generate considerable osmotic pressure on the polymeric membrane 202 as water moves through the membrane into the hydrogel.

The via 110 allows the polymeric membrane to seamlessly adhere to the sensor device. The adhesion trench(es) 122a (and 122b) and the resulting seamless adhesion of the polymeric membrane 202 to the sensor device 100 prevents the osmotic pressure created by the hydrogel buffer solution 204 from causing the hydrogel buffer solution from leaking out from under the polymeric membrane 202 and forming an electrical short circuit path around the membrane.

Figure 3:
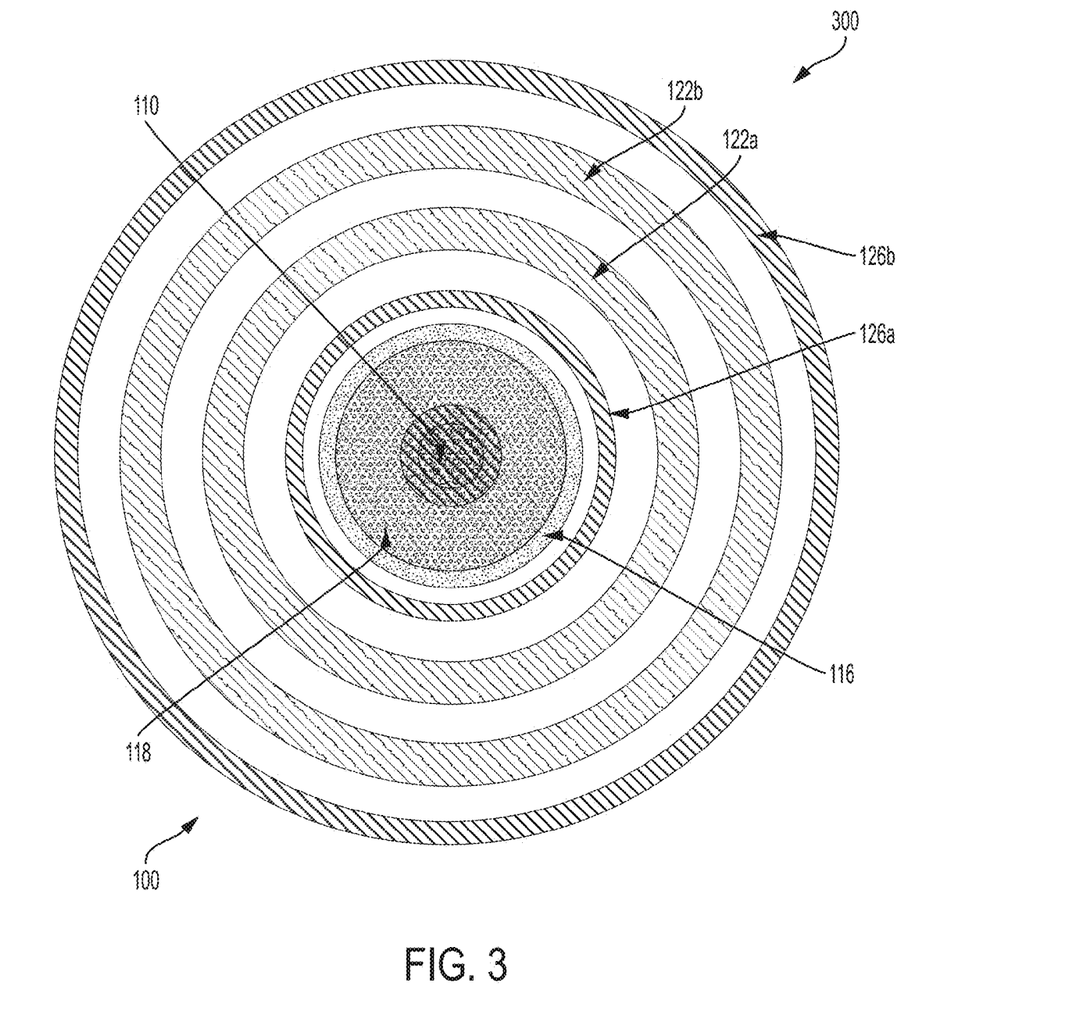
FIG. 3 is a schematic diagram of a top-down view of a sensor device in accordance with embodiments of the present disclosure.

FIG. 3 is a schematic diagram 300 of a top-down sectional illustration of a sensor device 100 in accordance with embodiments of the present disclosure. The diagram 300 shows an illustration of a top-down and sectional view of the sensor device 100. At the center is the via 110. Above the via 110 is the platinum disk 118. Above the platinum disk 118 is the silver/silver chloride electrode 116. Around the electrode 116 is the first polyimide ring 126a. Adhesion trenches 122a and 122b surround the first polyimide ring 126a. The second polyimide ring 126b surrounds the adhesion trenches 122a and 122b.

Figure 4:
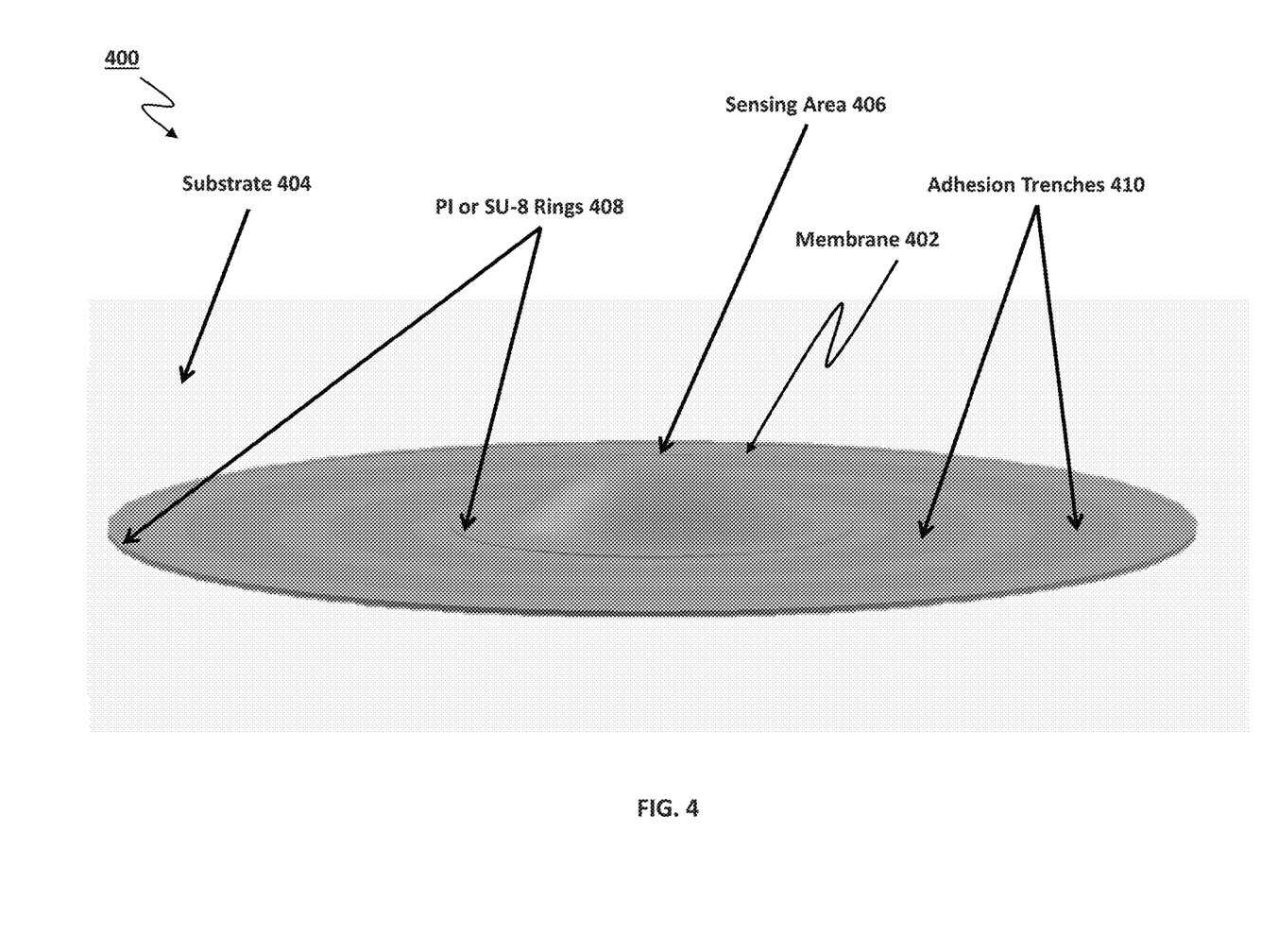
FIG. 4 is a schematic diagram of a chemical sensor with a membrane having full circumferential adhesion to a substrate in accordance with embodiments of the present disclosure.

FIG. 4 is a schematic diagram 400 of a chemical sensor with a membrane 402 having full circumferential adhesion to a substrate 404. The membrane 402 is shown to be in contact with the substrate 404, a portion of which is shown in FIG. 4. The membrane 402 covers the various structures that form the chemical sensor 400, with the exception of backside contacts and backside passivation layers (i.e., the membrane covers all of the components of the chemical sensor on the sensor-side of the substrate). For example, the membrane 402 encloses a sensing area 406 that can include the hydrogel internal filling solution, as well as the metal contact layers described above. The membrane 402 also covers the SU-8 or polyimide ring(s) (shown as rings 408 in FIG. 4). The membrane 402 also covers the adhesion trenches 410. Noteworthy is that FIG. 4 illustrates that the membrane 402 makes a full circumferential adhesion to the first passivation layer.

Figure 5A:
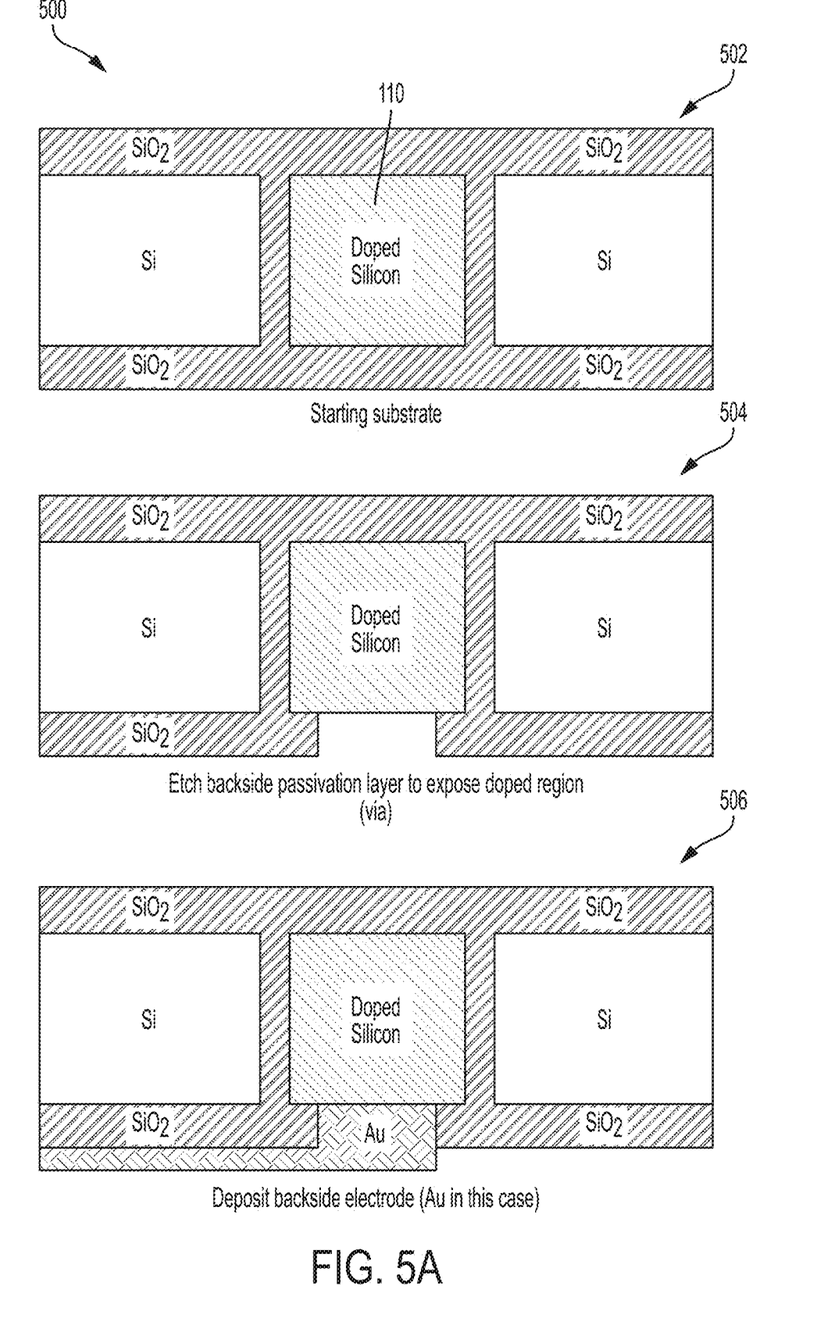
FIGS. 5A-B are schematic diagrams of a process flow for forming a backside electrode on the sensor device in accordance with embodiments of the present disclosure.
Figure 5B:
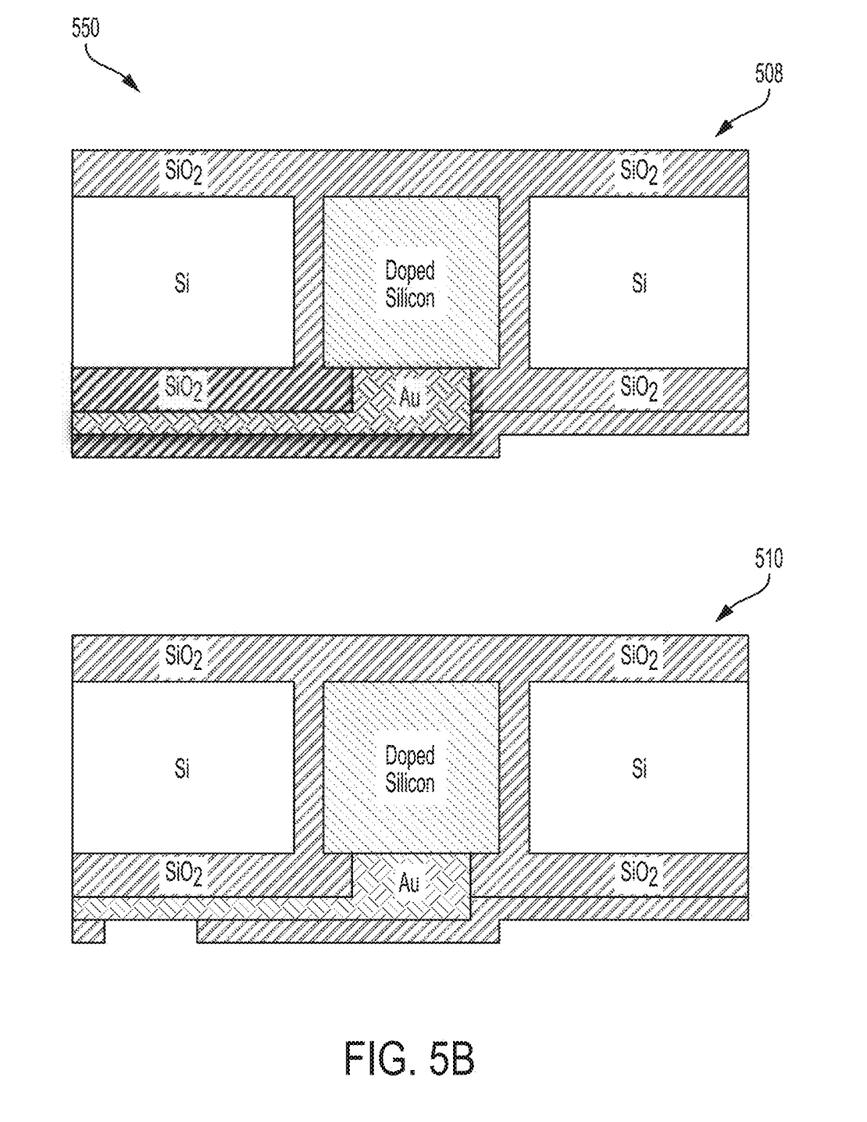

FIGS. 5A-B are schematic diagrams 500 and 550 of a process flow for forming a backside electrode on the sensor device in accordance with embodiments of the present disclosure. Starting with FIG. 5A, FIG. 5A is a schematic process flow diagram 500 showing a portion of the process steps for forming a backside electrode. The starting silicon substrate can include the sensor-side first passivation layer of silicon dioxide, a backside passivation layer of silicon dioxide, and an electrically isolated doped region that can serve as a via (502). The electrically isolated doped region can be electrically isolated from the rest of the substrate (which can also be doped) by a passivation layer, such as an SiO2 layer). The backside passivation layer can be etched using photolithographic techniques to expose the via (504). A metal, such as gold, is deposited on the backside of the sensor device and patterned using photolithographic techniques to form an electrode (506) making an electrical connection from the electrically isolated doped region (via) to a bonding pad.

Turning to FIG. 5B, FIG. 5B is a schematic process diagram 550 showing a portion of the process steps for forming a backside electrode. A protective passivation layer (for example silicon dioxide or silicon nitride) can be formed on the backside of the substrate to protect the backside and to protect the backside electrode (508). The protective passivation layer can be etched to reveal the metal backside electrode in a location offset from the electrically isolated doped region to form an offset bonding pad (510).

The through silicon via (TSV) (i.e., the electrically isolated doped region between the sensor side of the substrate and the backside of the substrate) can be isolated from the rest of the substrate by a TSV passivation layer. This passivation layer can be an SiO2 layer formed by forming an annular ring in the substrate through etching techniques and oxidizing the resulting cavity between the TSV and the substrate.

Figure 6A:
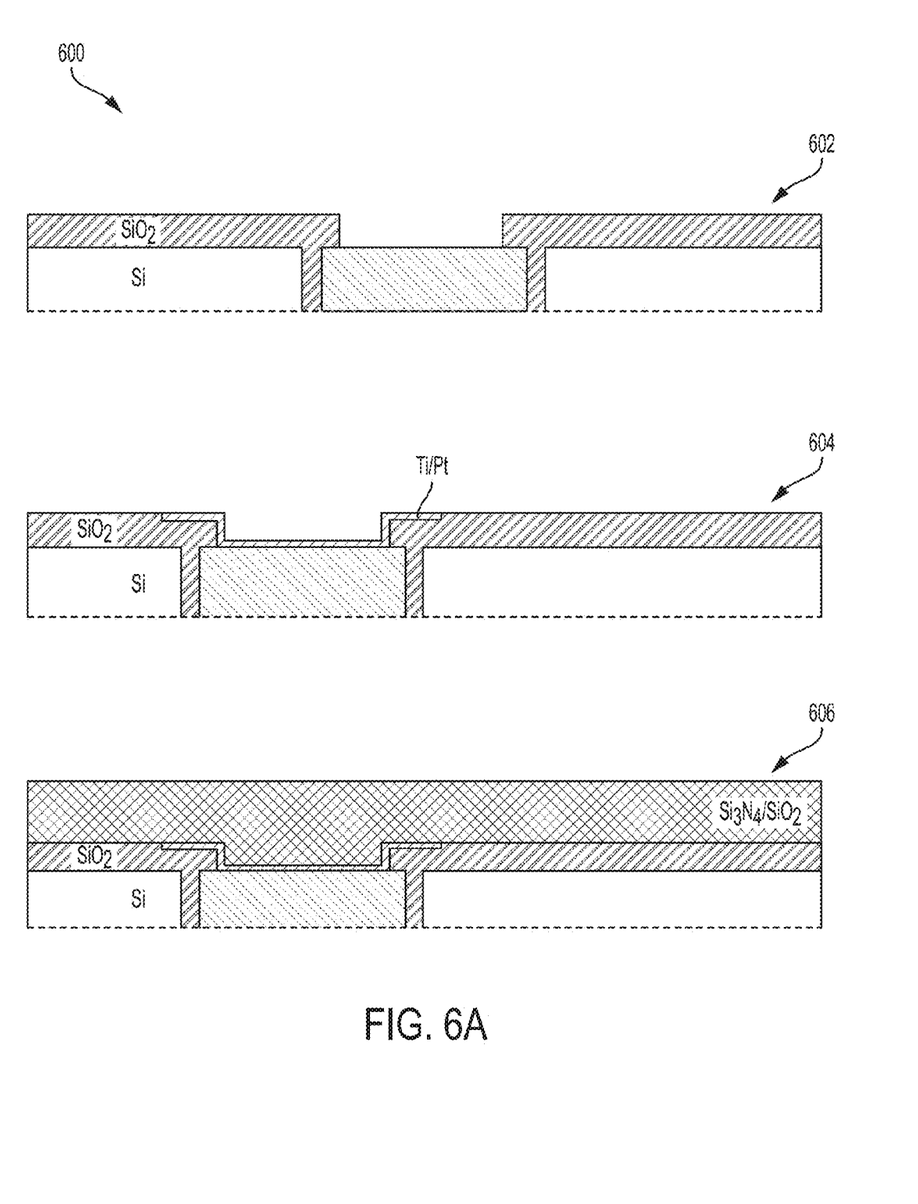
FIGS. 6A-C are schematic diagrams of a process flow for forming a chemical sensor with a membrane having full circumferential adhesion to a substrate in accordance with embodiments of the present disclosure.
Figure 6B:
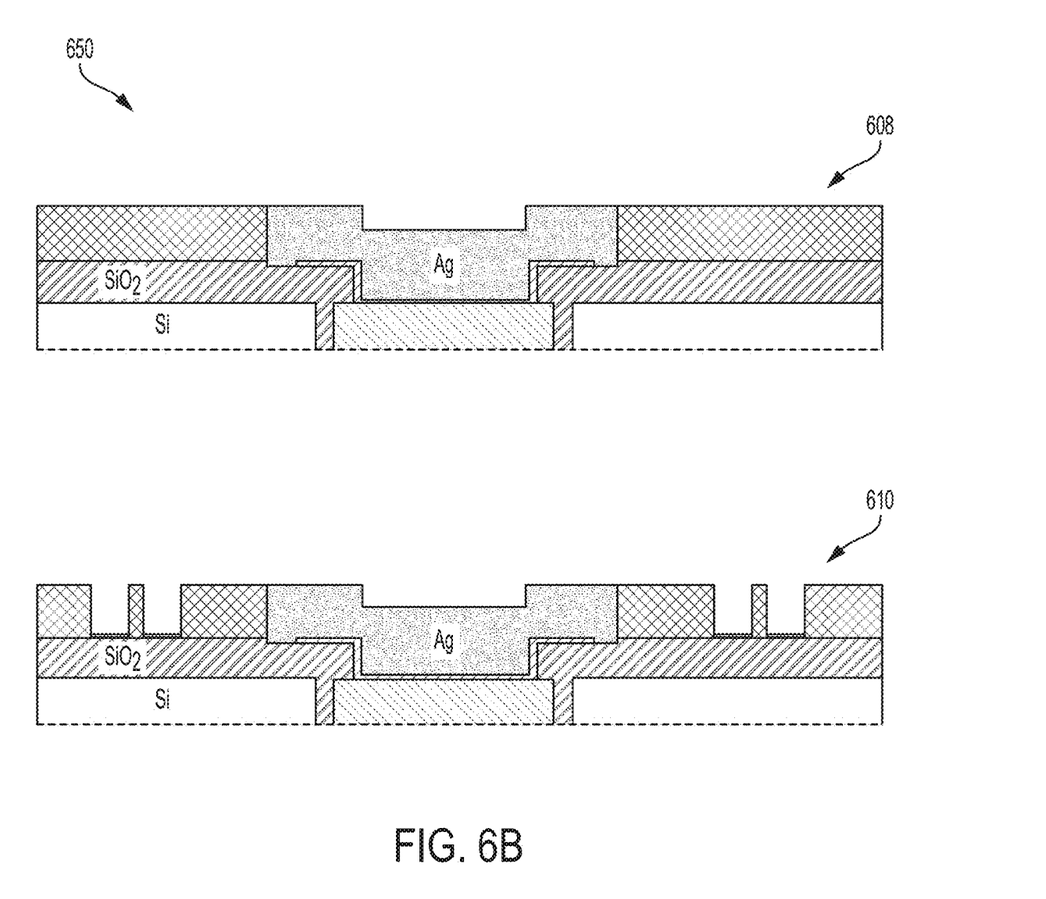
Figure 6C:
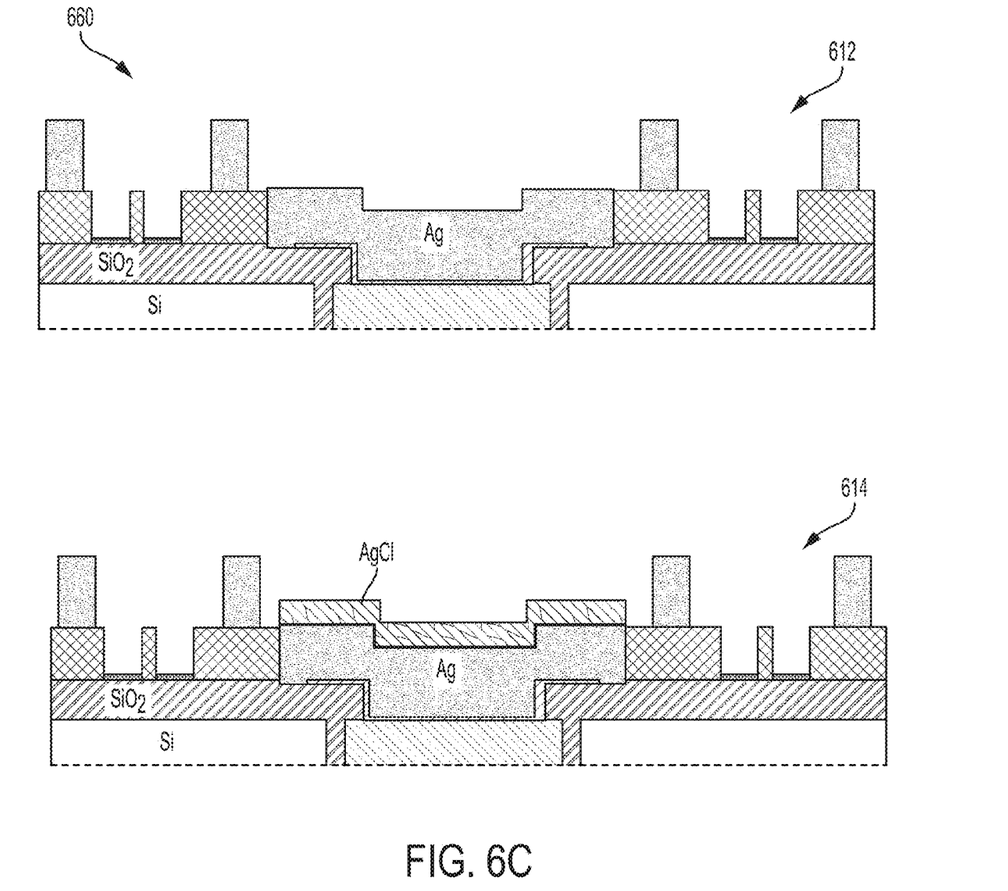

FIGS. 6A-C are schematic diagrams of a process flow for forming a chemical sensor with a membrane having full circumferential adhesion in accordance with embodiments of the present disclosure. FIG. 6A is a schematic process flow diagram 600 for a first set of process steps for forming a chemical sensor with a membrane having full circumferential adhesion in accordance with embodiments of the present disclosure. The sensor-side first passivation layer ($SiO_2$) can be etched using photolithographic techniques to expose the core of the electrically isolated doped region (via) (602). A platinum disk can be formed through photolithography and deposition to cover the contact to the via (604). A sensor-side second passivation layer can be deposited on the sensor side first passivation layer ($SiO_2$) and on the platinum disk (606). The sensor-side second passivation layer can be silicon nitride and can include a top layer of silicon dioxide.

FIG. 6B is a schematic process flow diagram 650 for a second set of process steps for forming a chemical sensor with a membrane having full circumferential adhesion in accordance with embodiments of the present disclosure. The sensor-side second passivation layer can be etched to expose the platinum disk. A metal, such as silver, can be deposited on the platinum to create an electrical connection with the via (608). The adhesion trench can be etched into the sensor-side second passivation layer (e.g., using photolithographic techniques) (610). One or more adhesion trenches can be etched. The sensor-side second passivation layer is etched to expose the underlying sensor-side first passivation layer ($SiO_2$). In some embodiments, an adhesion promoting material can be formed in the trench to promote polymeric membrane adhesion to the surface of the sensor device. The adhesion promoting material can include silane or a silanol or other known adhesion promoting material.

FIG. 6C is a schematic process flow diagram 660 for a third set of process steps for forming a chemical sensor with a membrane having full circumferential adhesion in accordance with embodiments of the present disclosure. High aspect-ratio photo polymer, such as polyimide or SU-8 can be patterned into rings on the sensor-side second passivation layer (612). The polymer rings can be formed by techniques such as those described in U.S. Pat. No. 6,764,652, filed Jan. 24, 2001 and U.S. Pat. No. 7,438,851, filed Apr. 30, 2004, the contents of which are incorporated by reference in its entirety. A first polymer ring can be formed adjacent to the electrode. A second polymer ring can be formed having a larger diameter than the first polyimide ring.

The silver deposited on the platinum disk can undergo chloridization to form the silver/silver chloride electrode (614). Chloridization can be achieved by submerging the substrate in NaOCl or other chloridizing solution. The result is a silver/silver chloride electrode that can be used as the sensor-side electrode for the sensor device.

Aspects described in this disclosure can employ thin-film fabrication techniques to create the devices and structures described herein, and to achieve advantages that are described herein and that are readily apparent to those of skill in the art.

Advantages of the present disclosure are readily apparent. Advantages of using the through-silicon via to connect to the micro ion-selective electrode may include the following:

Full circumference adhesion trenches can be cut through the silicon nitride passivation layer to silicon dioxide, which has sites to which the polymeric membrane can be covalently bonded. This covalent bonding gives the polymeric membrane good adhesion to the surface all the way around, preventing leakage paths between the internal filling solution (hydrogel buffer solution) and the solution under test, which would render the sensor unusable. The use of an adhesion promoter can increase the adhesion by forming stronger covalent bonds with the polymeric membrane.

In the current disclosure, the bonding pads for all of the sensor connections (not just the ion-selective electrodes) can be on the back side of the chip, which eliminates a major challenge of building micro chemical sensors: insulating the bonding wires from the test solution. In a conventional solid-state chemical sensor, bond wires connect the chip to a printed circuit board, and all of the conductors from the chip to the board and on the PCB must be encapsulated so that they have extremely high impedance to the solution under test.

The micro ISEs have very high impedance, so any leakage path can push them out of equilibrium, causing errors. The micro ion-selective electrodes (ISEs) are no longer subject to failure due to pin-hole defects in the silicon nitride passivation layer, because interconnect wires on the front side of the chip are eliminated.

While certain embodiments have been described in detail, those familiar with the art to which this disclosure relates will recognize various additional and/or alternative designs, embodiments, and process steps for making and using the sensor device as described by the following claims.

What is claimed is:

1. A sensor device comprising:
    a silicon substrate comprising a sensor-side and a backside, the backside on an opposite surface of the silicon substrate from the sensor-side;
    the sensor-side comprising:
        a sensor-side electrode;
        a first passivation layer disposed on the silicon substrate;
        a second passivation layer on the first passivation layer and adjacent to the sensor-side electrode, the second passivation layer comprising an adhesion trench exposing a portion of the first passivation layer, and a polyimide ring disposed on the second passivation layer;
    the backside comprising:
        a backside electrode on the backside of the silicon substrate; and
    the silicon substrate comprising a through-silicon via (TSV) electrically connecting the sensor-side electrode and the backside electrode.

2. The sensor device of claim 1, wherein the first passivation layer comprises silicon dioxide.

3. The sensor device of claim 1, wherein the second passivation layer comprises one or both of silicon nitride or silicon dioxide.

4. The sensor device of claim 1, wherein the sensor-side electrode comprises silver chloride on silver.

5. The sensor device of claim 1, wherein the backside electrode comprises gold.

6. The sensor device of claim 1, wherein the TSV comprises p-type doped silicon insulated from the rest of the substrate.

7. The sensor device of claim 6, wherein the TSV is insulated from the silicon substrate by a passivation layer between the p-type doped silicon TSV and the silicon substrate.

8. The sensor device of claim 1, wherein the polyimide ring defines a first diameter, and wherein the adhesion trench defines a second diameter greater than the first diameter.

9. The sensor device of claim 1, further comprising a hydrogel buffer solution disposed on the sensor-side electrode within the polyimide ring.

10. The sensor device of claim 1, wherein the polyimide ring is a first polyimide ring, the sensor device comprising a second polyimide ring surrounding the adhesion trench and the first polyimide ring.

11. The sensor device of claim 10, further comprising a polymeric membrane covering the sensor-side electrode and the adhesion trench, wherein the polymeric membrane is contained within the second polyimide ring.

12. The sensor device of claim 11, wherein the polymeric membrane comprises ionophores.

13. The sensor device of claim 11, wherein the polymeric membrane comprises an ion selective membrane.

14. The sensor device of claim 11, wherein the polymeric membrane contacts the first passivation layer within the adhesion trench.

15. The sensor device of claim 11, further comprising an adhesion layer disposed on the portion of the first passivation layer exposed within the adhesion trench, wherein the polymeric membrane is in contact with the adhesion layer.

16. A sensor device comprising:
 a substrate comprising a sensor-side and a backside, the backside on an opposite surface of the substrate from the sensor-side;
 the sensor-side comprising:
  a sensor-side electrode;
  a first passivation layer disposed on the substrate; and
  a second passivation layer on the first passivation layer and adjacent to the sensor-side electrode, the second passivation layer comprising an adhesion trench exposing a portion of the first passivation layer,
 the backside comprising:
  a backside electrode on the backside of the substrate; and
 the substrate comprising a through-substrate via electrically connecting the sensor-side electrode and the backside electrode.

17. The sensor device of claim 16, further comprising a ring disposed on the second passivation layer, the ring comprising one of SU-8 or polyimide.

18. The sensor device of claim 16, wherein the substrate comprises one of silicon or glass or ceramic.

19. The sensor device of claim 17, wherein the ring defines a first diameter, and wherein the adhesion trench defines a second diameter greater than the first diameter.

20. The sensor device of claim 17, further comprising a hydrogel buffer solution disposed on the sensor-side electrode within the ring.

21. The sensor device of claim 17, wherein the ring is a first ring, the sensor device comprising a second ring surrounding the adhesion trench and the first ring.

22. The sensor device of claim 21, further comprising a polymeric membrane covering the adhesion trench and contained within the second ring.

* * * * *